United States Patent [19]

Lambert et al.

[11] Patent Number: 4,908,375

[45] Date of Patent: Mar. 13, 1990

[54] FUNGICIDAL COMPOSITIONS BASED ON NICOTINIC DERIVATIVES

[75] Inventors: Claude Lambert, Lyon; Regis Pepin, Rilleux La Pape, both of France

[73] Assignee: Rhone-Poulenc Agrochimie, Lyon, France

[21] Appl. No.: 217,327

[22] Filed: Jul. 11, 1988

[30] Foreign Application Priority Data

Jul. 10, 1987 [FR] France .................. 87 10175

[51] Int. Cl.$^4$ .................. C07D 417/12; A61K 31/455
[52] U.S. Cl. .................. 514/342; 546/280; 546/256; 514/333
[58] Field of Search .................. 546/280, 256; 514/342, 514/333

[56] References Cited

U.S. PATENT DOCUMENTS 4,552,886 11/1985 Krumkalns et al. .................. 514/342

FOREIGN PATENT DOCUMENTS 3539476 5/1987 Fed. Rep. of Germany .

Primary Examiner—Jane T. Fan
Attorney, Agent, or Firm—Burns, Doane, Swecker & Mathis

[57] ABSTRACT

Nicotinic derivatives. They are of the formula

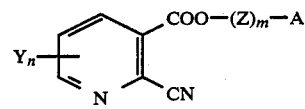

with:
 A = thiazolyl radical, illustrated where appropriate,
 Z = methylene,
 m = 1 to 4,
 y = H, hal, alkyl (1-4C), alkoxy (1-4C),
 n = 1 to 3

Fungicidal products for agriculture.

9 Claims, No Drawings

FUNGICIDAL COMPOSITIONS BASED ON NICOTINIC DERIVATIVES

The present invention relates to fungicidal compositions based on nicotinic derivatives, new nicotinic derivatives and use of nicotinic derivatives for controlling fungal diseases of plants, and especially against pyriculariosis of rice.

The subject of the invention is, more especially, the fungicidal compositions which are characterized in that they contain, as active substance, at least one compound of the formula:

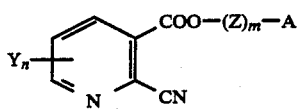  (I)

in which:

A is a thiazolyl radical having one of the formulae:

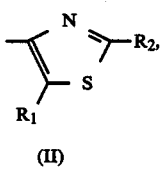 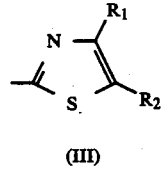 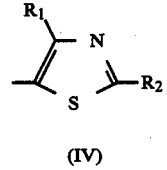
    (II)           (III)          (IV)

in which $R_1$ and $R_2$, which may be identical or different, are:

either a hydrogen atom, or a linear or branched alkyl or alkenyl radical having 1 to 18 carbon atoms, unsubstituted or substituted with a phenyl or phenoxy in which the phenyl ring can be substituted with one to five substituents chosen from the group comprising a halogen atom and an alkyl or alkoxy radical having 1 to 4 carbon atoms, or a phenyl radical, unsubstituted or substituted with one to five substituents chosen from the group comprising a halogen atom and an alkyl or alkoxy radical having 1 to 4 carbon atoms, or a pyridyl or thienyl radical, or an amino group, unsubstituted or substituted with at least one alkyl or alkoxy radical having 1 to 4 carbon atoms, phenylaminocarbonyl radical, alkylcarbonyl radical or phenylcarbonyl radical in which the phenyl is unsubstituted or substituted with one to five substituents chosen from the group comprising a halogen atom and an alkyl or alkoxy radical having 1 to 4 carbon atoms, Z is a methylene radical, optionally substituted, m is an integer from 1 to 4, and preferably 1 or 2, Y is a halogen atom or an alkyl or alkoxy radical having 1 to 4 carbon atoms, and n is an integer from 0 to 3.

The preferred compounds have the formula I in which A has the formula II, more especially those in the formula of which $R_2$ is an alkyl radical having 1 to 4 carbon atoms or a phenyl radical which is unsubstituted or substituted with 1 to 3 substituents chosen from the group comprising a chlorine atom, a methyl or ethyl radical or a methoxy or ethoxy radical.

The derivatives of the formula I may be obtained according to several processes: first, it is possible to react a compound of formula V with a suitable thiazolylalkyl halide according to the scheme (process A):

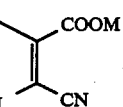

(V)

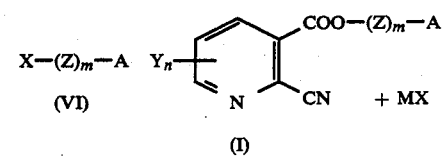

in which M is an alkali metal atom, X a halogen atom and the other substituents have the same meaning as above.

The reaction is performed in an aliphatic or aromatic solvent medium such as, e.g., hydrocarbons, optionally halogenated (e.g. toluene), or amides, ketones or nitriles (e.g. acetonitrile). Advantageously, the reaction is peformed in the presence of a catalyst of the phase transfer catalyst type, such as, e.g., tris(3,6-dioxaheptyl)amine (TDA-1) or 18-crown-6 ether.

It is also possible to react a compound of the formula V with a chlorinating agent to give an acid chloride derivative VII, which is reacted with an alcohol according to the scheme (process B):

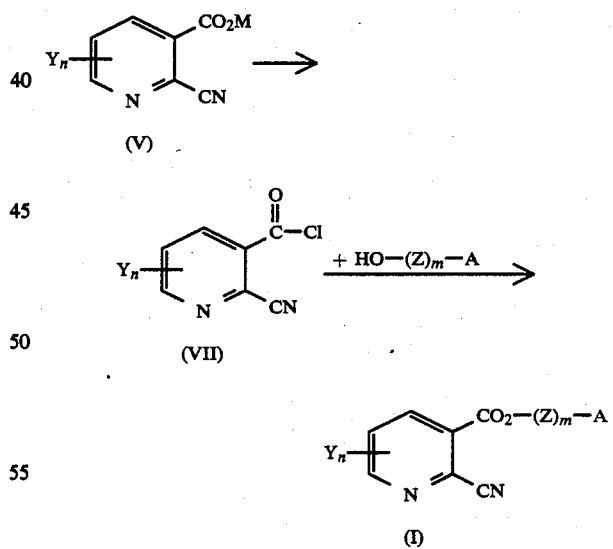

The treatment of V with a chlorinating agent, such as phosgene, oxalyl chloride or thionyl chloride, in an aliphatic solvent such as a chloroalkalne, yields the derivative VII. The latter is converted to the compound I by reaction with the appropriate alcohol $HO-(Z)_m A$ in the presence of an organic base such as, e.g., pyridine.

It is also possible to perform a transesterification according to the scheme (process C):

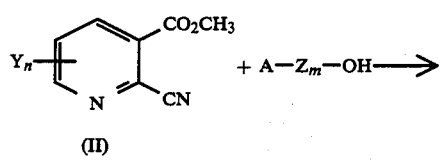

(II)

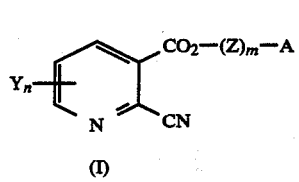

(I)

The reaction is performed in an aromatic solvent such as, e.g., toluene, in the presence of a catalytic amount of a base such as sodium methylate, with distillation of the methanol/solvent azeotrope as the methanol forms.

The examples which follow illustrate the preparation of the compounds according to the invention and their fungicidal properties. The structure of these compounds was verified by NMR spectrography.

EXAMPLE 1

(2-Methyl-4-thiazolyl)methyl 2-cyanonicotinate (Method A) (Compound 1)

A mixture of potassium 2-cyanonicotinate (4.1 g; 0.022 mole), 4-chloromethyl-2-methylthiazole (2.95 g; 0.02 mole) and 18-crown-6-ether (0.13 g; 0.0005 mole) in acetonitrile (50 cc) is brought to reflux for 8 hours. The solvent is then evaporated off and the residue taken up in water and extracted with dichloromethane. After drying, evaporation of the dichloromethane and purification by chromatography on a silica column, Compound 1(2.12 g; 41%; m.p. 93° C.) is obtained.

EXAMPLE 2

[2-(3-chlorophenyl)-4-thiazolyl]methyl 2-cyanonicotinate (Method C) (Compound 2)

Sodium methylate (0.11 g; 0.002 mole) is added to a solution of methyl 2-cyanonicotinate (3.24 g; 0.02 mole) and 2-(3-chlorophenyl)-4-(hydroxymethyl)thiazole (4.96 g; 0.022 mole) in toluene (100 cc). The methanol/toluene azeotrope is distilled off and the toluene is then evaporated off. The residue is treated with water. The precipitate formed is filtered off, washed with water and then dried. Compound 2 (1.8 g; 25% m.p. 130° C.) is obtained.

EXAMPLE 3

Working according to the procedure of Example 1 or 2, the following compounds are obtained, the formula and physicochemical properties of which are recorded in the following table:

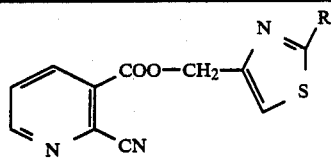

| no | R | m.p. °C. | method |
|---|---|---|---|
| 3 | ![Cl, Cl phenyl] | 189 | 2 |
| 4 | ![OC2H5 phenyl] | 125 | 2 |
| 5 | ![thiophene] | 187 | 2 |
| 6 | —CH2—O—[CH3, Cl phenyl] | 151 | 1 |
| 7 | ![Cl phenyl] | 150 | 2 |
| 8 | —CH2—[thiophene] | 78.5 | 1 |

EXAMPLE 4

The procedure is as in Example 2, replacing 4-chloromethyl-2-methylthiazole by an equimolar amount of 5-(2-chloroethyl)-4-methylthiazole. A compound (5.5 g) of m.p. 88° C. is obtained, corresponding to 2-(4-methyl-5-thiazolyl)ethyl 2-cyanonicotinate.

EXAMPLE 5

Greenhouse Test on Pyricularia oryzae

Rice plants in pots (variety Marcheti rosa), 10 cm high, are treated by sprinkling the soil with an aqueous suspension containing:
the test product (30 mg)
a surfactant (15 mg), a condensate of ethylene oxide (20 moles) with sorbitan monooleate, and
water (q.s. 30 ml).

This suspension, applied to square pots of side 7 cm, corresponds to a dose of approximately 60 kg/ha of active substance. The soil is allowed to absorb the product. A part of the rice plants was not treated, to serve as controls. After 24 hours following the treatment, all the rice plants are contaminated with a suspension of Pyricularia oryzae spores, obtained by scraping an in vitro culture, by spraying onto the leaves in the proportion of 5 cc of suspension per pot. The pots are left to incubate for 48 h at 25° C. and at 100° relative humidity.

The plants are then placed in an observation cell in the greenhouse.

Observation is performed after 8 days following the contamination.

Under these conditions, it is observed that, at a dose of 1,000 ppm, an at least 80% inhibition of the fungus is obtained with Compounds 1, 2 and 4.

This difference shows clearly the systemic fungicidal properties of the compounds according to the invention, and their exceptional action on pyriculariosis of rice.

The products according to the invention may be employed alone, dispersed or dissolved in water or in the form of compositions which can also contain any other type of ingredients such as, e.g., protective colloids, adhesives, thickeners, thixotropic agents, penetrating agents, stabilizers, sequestering agents, and the like, as well as other known active substances having pesticidal (in particular, insecticidal or fungicidal) properties, or have properties promoting plant growth (in particular, fertilizers) or having plant growth regulatory properties. More generally, the compounds according to the invention may be combined with all solid or liquid additives corresponding to the customary techniques of preparing formulations.

These doses for application in the case of a use of the compounds according to the invention as fungicides can vary within wide limits, in particular according to the virulence of the fungi and the climatic conditions.

Generally speaking, compositions containing 0.5 to 5,000 ppm of active substance are very suitable; these values are indicated for the compositions ready for application. Ppm denotes "parts per million". The range from 0.5 to 5,000 ppm corresponds to a range from $5 \times 10^{-5}$ to 0.5% (percentages by weight).

As regards the compositions suitable for storage and transport, these contain, more advantageously, from 0.5 to 95% (by weight) of active substance.

Thus, the compositions for agricultural use according to the invention can hence contain the active substances according to the invention within very wide limits, ranging from $5 \times 10^{-5}$% to 95% (by weight).

According to what has already been stated, the compounds according to the invention are generally combined with carriers and optionally with surfactants.

The term "carrier" in the present description denotes a natural or synthetic organic or inorganic substance with which the active substance is combined in order to facilitate its application on the plant, on the seeds or on the soil. This carrier is hence gradually inert, and it must be agriculturally acceptable, in particular on the plant being treated. The carrier can be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

The surfactant can be an emulsifying, dispersant or wetting agent of the ionic or nonionic type. There may be mentioned, e.g., polyacrylic acid salts, lignosulphonic acid salts, salts of phenolsulphonic or naphthalenesulphonic acids, polycondensates of ethylene oxide with fatty alcohols or with fatty acids or with fatty amines, substituted phenols (in particular alkylphenols or arylphenols), salts of sulphosuccinic acid esters, taurine derivatives (in particular, alkyl taurates), and phosphoric acid esters of alcohols or phenols polycondensed with ethylene oxide. The presence of at least one surfactant is generally essential when the active substance and/or the inert carrier is/are insoluble in water and when the vehicle for the application is water.

The compositions used in the invention can be in fairly diverse, solid or liquid forms.

As solid forms of the compositions, dusting powders (having a content of active substances which can range up to 100%) may be mentioned.

As liquid forms of the compositions, or forms designed to make liquid compositions at the time of application, there may be mentioned solutions, especially water-soluble concentrates, emulsifiable concentrates, emulsions, flowables, aerosols, wettable powders (or powder for spraying), granules and pastes.

The emulsifiable or soluble concentrates most often comprise 10 to 80% of active substance, the ready-for-use emulsions or solutions containing, for their part, 0.001 to 20% of active substance. In addition to the active substance and the solvent, the emulsifiable concentrates can contain, when necessary, a suitable cosolvent and suitable additives (from 2 to 20%) such as stabilizers, surfactants, in particular emulsifiers, penetrating agents, corrosion inhibitors, colourings and adhesives.

EXAMPLE (EC 1)

| | |
|---|---|
| Active substances (compound 1) | 400 g/l |
| Alkali metal dodecylbenzenesulphonate | 24 g/l |
| Condensate of nonylphenol with 10 moles of ethylene oxide | 16 g/l |
| Cyclohexanone | 200 g/l |
| Aromatic solvent | q.s. 1 liter |

According to another formula for an emulsifiable concentrate, the following are used:

EXAMPLE (EC2)

| | |
|---|---|
| Active substances (compound 2) | 250 g/l |
| Epoxide-treated vegetable oil | 25 g/l |
| Mixture of alkylaryl sulphonate and ether of polyglycol and fatty alcohol | 100 g/l |
| Dimethylformamide | 50 g/l |
| Xylene | q.s. 1 liter |

From these concentrates, emulsions of any desired concentration, which are especially suitable for application to crops, may be obtained by dilution with water.

The flowables, which are also applicable by spraying, are prepared so as to obtain a stable fluid product which does not deposit, and they usually contain active substance (from 10 to 75%), surfactants (from 0.5 to 15%), thixotropic agents (from 0.1 to 10%), suitable additives (from 0 to 10%) such as antifoams, corrosion inhibitors, stabilizers, penetrating agents and adhesives, and, as carrier, water or an organic liquid in which the active substance is only slightly soluble or is insoluble: some organic solid substances or inorganic salts may be dissolved in the carrier in order to assist in preventing sedimentation or as antifreeze for the water.

By way of example, there follows the composition of several aqueous suspensions according to the invention:

EXAMPLE SP 1

An aqueous suspension is prepared, comprising:

| | |
|---|---|
| Active substance (Compound No. 1) | 500 g/l |
| Wetting agent (polycondensate of $C_{13}$ | 10 g/l |

| | |
|---|---|
| synthetic alcohol with ethylene oxide) | |
| Dispersant agent (salified condensate of polyarylphenol phosphate with ethylene oxide | 50 g/l |
| Antifreeze (propylene glycol) | 100 g/l |
| Thickener (polysaccharide) | 1.6 g/l |
| Biocide (methyl 4-hydroxybenzoate, sodium salt) | 3.3 g/l |
| Water | q.s 1 liter |

A fluid flowable is thereby obtained.

EXAMPLE SP 2—AQUEOUS SUSPENSION

An aqueous suspension is prepared, comprising:

| | |
|---|---|
| Active substance (Compound 2) | 100 g/l |
| Wetting agent (polycondensate of alkylphenol with ethylene oxide) | 5 g/l |
| Dispersant agent (Na naphthalenesulphonate) | 10 g/l |
| Antifreeze (propylene glycol) | 100 g/l |
| Thickener (polysaccharide) | 3 g/l |
| Biocide (formaldehyde) | 1 g/l |
| Water | q.s. 1 liter |

EXAMPLE SP 3—AQUEOUS SUSPENSION

An aqueous suspension is prepared, comprising:

| | |
|---|---|
| Active substance (Compound No. 4) | 250 g/l |
| Wetting agent (polycondensate of $C_{13}$ synthetic alcohol with ethylene oxide) | 10 g/l |
| Dispersant agent (sodium lignosulphonate) | 15 g/l |
| Antifreeze (urea) | 50 g/l |
| Thickener (polysaccharide) | 2.5 g/l |
| Biocide (formaldehyde) | 1 g/l |
| Water | q.s. 1 liter |

The wettable powders (or powder for spraying) are usually prepared so that they contain 20 to 95% of active substance, and they usually contain, in addition to the solid carrier, a wetting agent (from 0 to 5%), a dispersant agent (from 3 to 10%) and, when necessary, from 0 to 10% of one or more stabilizers and/or other additives such as penetrating agents, adhesives, or anti-caking agents, colourings, and the like.

By way of example, there follows the composition of several wettable powders.

EXAMPLE WP 1, WETTABLE POWDER

| | |
|---|---|
| Active substance (Compound No. 1 according to the invention) | 50% |
| Condensate of fatty alcohol with ethylene oxide (wetting agent) | 2.5% |
| Condensate of styrylphenol with ethylene oxide (dispersant agent) | 5% |
| Chalk (inert carrier) | 42.5% |

EXAMPLE WP 2: 10% STRENGTH WETTABLE POWDER

| | |
|---|---|
| Active substance (Compound No. 4) | 10% |
| Condensate of branched-type $C_{13}$ synthetic oxo alcohol with 8 to 10 ethylene oxide units (wetting agent) | 0.75% |
| Neutral calcium lignosulphonate (dispersant agent) | 12% |
| Calcium carbonate (inert filler) q.s. | 100% |

EXAMPLE WP 3: 75% STRENGTH WETTABLE POWDER CONTAINING the same ingredients as in the preceding example, in

| | |
|---|---|
| Active substance (Compound No. 2) | 75% |
| Wetting agent | 1.50% |
| Dispersant agent | 8% |
| Calcium carbonate (inert filler) q.s. | 100% |

EXAMPLE WP 4: 90% STRENGTH WETTABLE POWDER

| | |
|---|---|
| Active substance (Compound No. 1) | 90% |
| Condensate of fatty alcohol with ethylene oxide (wetting agent) | 4% |
| Condensate of styrylphenol with ethylene oxide (dispersant agent) | 6% |

EXAMPLE WP 5: 50% STRENGTH WETTABLE POWDER

| | |
|---|---|
| Active substance (Compound No. 4) | 50% |
| Mixture of anionic and nonionic surfactants (wetting agent) | 2.5% |
| Neutral sodium lignosulphonate (dispersant agent) | 5% |
| Kaolinic clay (inert carrier) | 42.5% |

To obtain these powders for spraying or wettable powders, the active substance is intimately mixed in suitable mixers with the additional substances, and the mixture is ground in mills or other suitable grinders. Powders for spraying are thereby obtained, the wettability and suspendibility of which are advantageous; they may be suspended in water at any desired concentration, and this suspension is very advantageously usable, especially for application on plant leaves.

The compounds according to the invention may be advantageously formulated in the form of water-dispersible granules which are also included within the scope of the invention.

These dispersible granules, generally having an apparent density of between 0.3 and 0.6, generally have a particle size of between approximately 150 and 2,000 and preferably between 300 and 1,500 microns.

The content of active substance (Compound No. 4) in these granules is generally between approximately 1% and 90%, and preferably between 25% and 90%.

The remainder of the granule is essentially composed of a solid filler and, optionally, of adjuvants endowing the granule with properties of dispersibility in water. These granules can be essentially of two different types, depending on whether the filler used is soluble or insoluble in water. When the filler is water-soluble, it can be inorganic and is preferably organic. Excellent results have been obtained with urea. In the case of an insoluble filler, the latter is preferably inorganic, such as, e.g., kaolin or bentonite. It is then accompanied by surfactants (in the proportion of 2 to 20% by weight of the granule), surfactant adjuvants of which more than one half consist of at least one dispersant agent, essentially anionic, such as a poly(alkyli metal or alkaline earth metal naphthalenesulphonate) or an alkali metal or alkaline earth metal lignosulphonate, the remainder consisting of nonionic or anionic wetting agents such as an alkali metal or alkaline earth metal alkylnaphthalenesulphonate.

Moreover, although this is not essential, it is possible to add other adjuvants such as antifoaming agents.

The granule according to the invention may be prepared by mixing the necessary ingredients followed by granulation according to several techniques that are known per se (bowl granulator, fluidized bed, atomizer, extrusion, and the like). The preparation is generally completed by a crushing followed by sieving to the particle size chosen within the limits mentioned above.

Preferably, it is obtained by extrusion, working as described in the examples below.

EXAMPLE DG 1

Dispersible Granules Containing 90% of Active Substance

Active substance (Compound No. 2; 90%) and urea beads (10%) are mixed in a mixer. The mixture is then ground in a toothed roll crusher. A powder is obtained which is moistened with water (approximately 8% by weight). The wet powder is extruded in a perforated roll extruder. A granule is obtained which is dried, then crushed and sieved, so as to retain, respectively, only the granules having a size of between 150 and 2,000 microns.

EXAMPLE DG 2

Dispersible Granules Containing 75% of Active Substance

The following constituents are mixed in a mixer:

| | |
|---|---|
| Active substance (Compound No. 1) | 75% |
| Wetting agent (sodium alkylnaphthalenesulphonate) | 2% |
| Dispersant agent (sodium polynaphthalenesulphonate) | 8% |
| Water-insoluble inert filler (kaolin) | 15% |

This mixture is granulated in a fluidized bed, in the presence of water, then dried, crushed and sieved so as to obtain granules having a size of between 0.16 and 0.40 mm.

These granules may be used alone, in solution or dispersion in water so as to obtain the desired dose. They may also be used for preparing combinations with other active substances, in particular fungicidal substances, the latter being in the form of wettable powders or of granules or aqueous suspensions.

As has already been stated, the dispersions and aqueous emulsions, e.g. compositions obtained by diluting with water a wettable powder or an emulsifiable concentrate according to the invention, are included within the general scope of the compositions that are usable in the present invention. The emulsions can be of the water-in-oil or oil-in-water type, and they can have a thick consistency like that of a "mayonnaise".

This process consists in applying on these plants an effective amount of a composition containing, as active substance, a compound according to the formula (I). "Effective amount" is understood to mean an amount sufficient to enable the fungi present on these plants to be controlled and destroyed. The doses for use can, however, vary within wide limits depending on the fungus to be combated, the type of crop and the climatic conditions, and depending on the compound used.

In practice, doses ranging from 1 g/hl to 500 g/hl, corresponding substantially to doses of active substance per hectare of 10 g/ha to 5,000 g/ha, approximately, generally give good results.

I claim:

1. A nicotinic compound of formula:

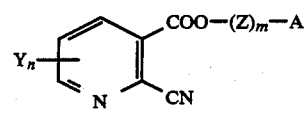

in which:

A is a thiazolyl radical having one of the formulae:

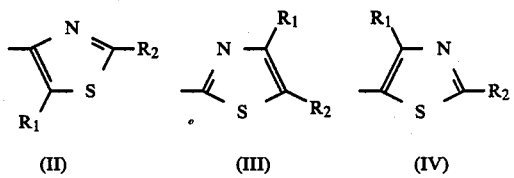

in which $R_1$ and $R_2$, which may be identical or different, are:

either a hydrogen atom, or a linear or branched alkyl or alkenyl radical having 1 to 18 carbon atoms, unsubstituted or substituted with a phenyl or phenoxy in which the phenyl ring can be substituted with one to five substituents selected from the group consisting of a halogen atom and an alkyl or alkoxy radical having 1 to 4 carbon atoms, or a phenyl radical, unsubstituted or substituted with one to five substituents selected from the group consisting of a halogen atom and an alkyl or alkoxy radical having 1 to 4 carbon atoms, or a pyridyl or thienyl radical, or an amino group, unsubstituted or substituted with at least one alkyl or alkoxy radical having 1 to 4 carbon atoms, phenylaminocarbonyl radical, alkylcarbonyl radical or phenylcarbonyl radical in which the phenyl is unsubstituted or substituted with one to five substituents selected from the group consisting of a halogen atom and an alkyl or alkoxy radical having 1 to 4 carbon atoms, Z is a methylene radical, m is an integer from 1 to 4, Y is a halogen atom or an alkyl or alkoxy radical having 1 to 4 carbon atoms, and n is an integer from 0 to 3.

2. The compound according to claim 1, in which A has the formula II.

3. The compound according to claim 2, in which n equals 1 or 2.

4. The compound according to claim 3, in which $R_2$ is an alkyl radical having 1 to 4 carbon atoms.

5. The compound according to claim 4, in which $R_2$ is a methyl.

6. The compound according to claim 1, in which $R_2$ is a phenyl substituted with 1 to 3 substituents selected from the group consisting of a chlorine atom, a methyl group, an ethyl group, a methoxy radical and an ethoxy radical.

7. The compound according to claim 1, wherein m is the integer 1 or 2.

8. A fungicidal composition for the protection of plants against fungal diseases, which contains, as an active substance, an effective fungicidal amount of a compound according to one of claims 1 to 6 and an inert carrier therefor.

9. A method for treating fungal diseases of plants, wherein an effective fungicidal amount of a compound according to one of claims 1 to 6 is applied to plants as an active substance.

* * * * *